United States Patent [19]

Wirt

[11] Patent Number: 4,925,327

[45] Date of Patent: May 15, 1990

[54] LIQUID APPLICATOR WITH METERING INSERT

[75] Inventor: David F. Wirt, Oak Grove Heights, Wis.

[73] Assignee: Minnesota Mining and Manufacturing Company, St. Paul, Minn.

[21] Appl. No.: 252,021

[22] Filed: Sep. 28, 1988

Related U.S. Application Data

[63] Continuation of Ser. No. 904,788, Sep. 4, 1986, abandoned, which is a continuation-in-part of Ser. No. 798,989, Nov. 18, 1985, abandoned.

[51] Int. Cl.$^5$ .................... A47L 13/17; A61M 35/00
[52] U.S. Cl. .................... 401/205; 401/132; 401/196; 604/3
[58] Field of Search ............ 401/132, 133, 134, 135, 401/196, 206, 207, 140, 205, 198, 199, 202; 604/3

[56] References Cited

U.S. PATENT DOCUMENTS

| | | |
|---|---|---|
| 348,403 | 8/1886 | Marsh . |
| 436,822 | 9/1890 | Booraem . |
| 715,296 | 12/1902 | Rickey . |
| 875,422 | 12/1907 | Garvey et al. . |
| 965,075 | 7/1910 | Cardinet . |
| 1,074,522 | 9/1913 | Nelson . |
| 1,497,229 | 6/1924 | Reeff . |
| 2,217,027 | 10/1940 | O'Brien .................... 137/69 |
| 2,244,939 | 6/1941 | Carlson .................... 285/2 |
| 2,260,500 | 10/1941 | Wylie .................... 285/2 |
| 2,529,036 | 11/1950 | Loewinsohn .................... 15/138 |
| 2,631,049 | 3/1953 | McGillis et al. .................... 285/122 |
| 2,744,661 | 5/1956 | Davis .................... 222/189 |
| 2,761,833 | 9/1956 | Ward .................... 210/24 |
| 2,807,288 | 9/1957 | Shea .................... 141/18 |
| 2,815,889 | 12/1957 | Stetz et al. .................... 222/189 |
| 2,820,234 | 1/1958 | Rigney .................... 15/136 |
| 2,853,727 | 9/1958 | Nadai .................... 401/202 |
| 3,129,452 | 4/1964 | Schwartzman .................... 15/566 |
| 3,132,370 | 5/1964 | Capezzuto .................... 401/202 X |
| 3,133,309 | 5/1964 | Miles .................... 401/202 X |
| 3,148,401 | 9/1964 | Gilchrist et al. .................... 15/566 |
| 3,156,272 | 11/1964 | Indrunas .................... 141/286 |
| 3,189,223 | 6/1965 | Mackal .................... 222/1 |
| 3,248,017 | 4/1966 | Allen .................... 222/189 |
| 3,324,855 | 6/1967 | Heimlich .................... 128/269 |
| 3,349,966 | 10/1967 | Schwartzman .................... 222/80 |
| 3,356,095 | 12/1967 | Tylle .................... 401/134 |
| 3,362,640 | 1/1968 | Fainman .................... 239/1 |
| 3,393,963 | 7/1968 | Nadai .................... 401/207 |
| 3,471,245 | 10/1969 | Schwartzman .................... 401/207 |
| 3,614,245 | 10/1971 | Schwartzman .................... 401/132 |
| 3,682,558 | 8/1972 | Miller .................... 401/200 |
| 3,756,472 | 9/1973 | Vos .................... 222/189 |
| 3,760,987 | 9/1973 | Meterhoefer .................... 222/153 |
| 3,774,609 | 11/1973 | Schwartzman .................... 128/269 |
| 3,830,241 | 8/1974 | Dye et al. .................... 128/349 R |
| 3,847,151 | 11/1974 | D'Alessandro .................... 128/269 |
| 3,876,314 | 4/1975 | Nehring .................... 401/133 |
| 3,891,331 | 6/1975 | Avery .................... 401/132 |
| 3,896,808 | 7/1975 | Sapur .................... 128/269 |
| 3,955,712 | 5/1976 | Santore .................... 222/80 |

(List continued on next page.)

FOREIGN PATENT DOCUMENTS

| | | |
|---|---|---|
| 60493 | 3/1913 | Austria .................... 401/202 |
| 180182 | 3/1906 | Fed. Rep. of Germany .................... 401/202 |
| 1086705 | 11/1953 | France . |
| 1205411 | 4/1958 | France . |
| 2119235A | 11/1983 | United Kingdom . |

*Primary Examiner*—Steven A. Bratlie
*Attorney, Agent, or Firm*—Donald M. Sell; Walter N. Kirn; Jennie G. Boeder

[57] ABSTRACT

A liquid applicator as provided which is particularly useful in applying pre-operative surgical scrubs or paints to skin. The article is provided with an inner layer of porous metering material and an outer layer of open-cell foam sponge material which regulate the flow of liquid therethrough to provide acceptable wetting of the foam sponge while preventing dripping therefrom. The applicator includes an air vent spaced from the applicator head to allow air to flow into the applicator while liquid is being dispensed.

12 Claims, 2 Drawing Sheets

U.S. PATENT DOCUMENTS

| | | | |
|---|---|---|---|
| 3,958,571 | 5/1976 | Bennington | 128/269 |
| 3,981,304 | 11/1976 | Sapur | 128/269 |
| 4,008,718 | 2/1977 | Pitesky | 128/218 R |
| 4,008,968 | 2/1977 | Hobbs | 401/207 |
| 4,078,865 | 3/1978 | Moser | 401/23 |
| 4,111,567 | 9/1978 | Berghahn et al. | 401/202 |
| 4,148,318 | 4/1979 | Meyer | 128/269 |
| 4,183,684 | 1/1980 | Avery, Jr. | 401/133 |
| 4,189,245 | 2/1980 | Bennett | 401/126 |
| 4,218,155 | 8/1980 | Weidner | 401/132 |
| 4,225,254 | 9/1980 | Holberg et al. | 401/119 |
| 4,229,116 | 10/1980 | Moore | 401/275 |
| 4,291,491 | 9/1981 | Maddock | 401/140 X |
| 4,329,990 | 5/1982 | Sneider | 128/239 |
| 4,342,522 | 8/1982 | Mackles | 401/214 |
| 4,415,288 | 11/1988 | Gordon et al. | 401/132 |
| 4,463,880 | 8/1984 | Kramer et al. | 222/189 |
| 4,484,827 | 11/1984 | Price, Jr. | 401/205 |
| 4,498,796 | 2/1985 | Gordon et al. | 401/132 |
| 4,507,111 | 3/1985 | Gordon et al. | 604/3 |
| 4,588,319 | 5/1986 | Niemeyer | 401/205 |
| 4,594,015 | 6/1986 | Pomares | 401/266 |

LIQUID APPLICATOR WITH METERING INSERT

This is a continuation of application Ser. No. 904,788, filed Sept. 4, 1986, now abandoned, which is a continuation-in-part of Ser. No. 798,989, filed Nov. 18, 1985, now abandoned.

TECHNICAL FIELD

This invention relates to liquid applicators having particular utility in the field of aspetic surgery preparation. More particularly, this invention relates to articles useful in applying pre-operative surgical scrubs or paints to skin.

BACKGROUND OF THE INVENTION

Antiseptic preparation of patients for surgery conventionally includes a 3-10 minute scrubbing of the affected area with a soap solution followed by the application of a water-soluble antiseptic paint solution. These solutions are generally applied with saturated sponges that are attached to a blade or held with forceps. The sponges are saturated by soaking in open pans of solution. Numerous devices have been developed in an attempt to prevent the dripping of solution associated with the original technique. Another goal was to reduce the time required for application of the antiseptic solution.

The most important problem associated with prior art devices developed to apply surgical prep solutions is the lack of control of the delivery of the fluid to the sponge in a manner that will prevent dripping. Additional problems encountered with such devices include manufacturing complexity, reliability of rupturable joints and inappropriate geometries.

U.S. Patent Nos. 4,415,288; 4,507,111; and 4,498,796 describe a device that includes a liquid-containing rupturable cylindrical cartridge which is slidable within a tubular handle having one or two hollow within a tubular handle having one or two No. 4,497,796, the spikes communicate to recesses bored or burned into the interior of the sponge to facilitate free flow and even distribution of the fluid. In order for fluid to flow by gravity from this device, air must be entrained into the cartridge through the sponge and at least one hollow spike. For the following two reasons, this is not a reliable and predictable means to control the rate of delivery of fluid to the sponge. First, as the sponge becomes wet its air permeability decreases thereby restricting the entrainment of air. Second, hollow tubes with sufficiently small inside diameters to effectively meter the fluid flow rate to prevent dripping tend to "air-lock" due to the surface tension of the liquid. An additional disadvantage of the design of this device is the recesses in the sponge. These recesses are an attempt to improve the predictability of air entrainment and fluid distribution, but add to the manufacturing costs.

The device described in U.S. Pat. No. 3,847,151 includes a sponge mounted on a nozzle extending from a hollow handle which contains an antiseptic solution. The solution is dispensed into the sponge when a rupturable joint in the nozzle is broken and external pressure is applied to the flexible handle. The problems associated with the design of this device include the unreliability of the rupturable joint and the lack of control of the fluid delivery into the sponge. Inherent mass production variability makes the fabrication of a reliable rupturable joint based on stress concentration difficult. After the nozzle is opened, it is very difficult, in practice, to deliver precisely the correct volume of fluid to saturate the sponge without dripping. In addition, as the sponge is wetted by the fluid, its ability to entrain air is diminished.

U.S. Pat. No. 4,148,318 describes a device that includes an antiseptic solution contained in an integral reservoir with a frangible cover. Spikes affixed to a recess in the sponge pierce the cover to release the solution. The disadvantage of this device and other devices that include liquid-containing ampoules, such as those described in U.S. Pat. Nos. 3,891,331 and 4,183,684, is the absence of a means to control the delivery of fluid to the sponge. The absence of a means to control the fluid flow rate to the sponge limits the volume of solution that can be delivered without dripping.

U.S. Pat. No. 4,342,522 describes a roll-on dispenser which includes a porous open-cell foam membrane deformable by an applicator ball to regulate the dispensation of controlled amounts of powders. The amount of material dispensed is dependent upon the porosity of the membrane and the porosity of the membrane is dependent upon the degree of its deformation by the ball upon operation of the dispenser.

SUMMARY OF THE INVENTION

This invention relates to an article useful as a dispenser for the application of a liquid to a surface comprising (a) a hollow elongate member having a major orifice at one end;

(b) a layer of unfoamed metering material disposed over the major orifice of the hollow elongate member the porous metering material having a reservoiring capacity of less than about 5.0 cc/gm and the layer capable of regulating the flow of liquid therethrough;

(c) a layer of sponge material disposed over the exterior surface of the layer of porous metering material; and (d) an air vent in the hollow elongate member capable of providing air flow between the exterior and interior of the hollow elongate member.

The current invention provides a means to reliably deliver in a short period of time a surgical prep solution to an applicator sponge without dripping. The applicator of the present invention controls the flow rate of liquid therein to the applicator sponge without the need for external operator manipulation. Unlike the devices of the prior art, the applicator of this invention provides control of the flow rate of liquid to the applicator sponge without squeezing the liquid container or compressing the applicator sponge. Although intended to apply modern, low viscosity, nonwater soluble, film-forming prep solutions, this device can be configured to apply a variety of solution composition, viscosities and volumes without compromising the fast wetting and no dripping features. The geometry of the device was designed to be compatible with modern antiseptic techniques. Because fabrication of the device utilizes high volume production processes, the manufacturing costs of the device are sufficiently inexpensive to permit disposable use.

DETAILED DESCRIPTION OF THE INVENTION

Figure 1:
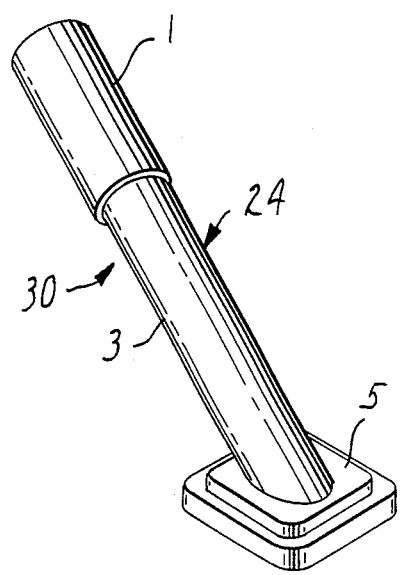
FIG. 1 is a perspective view of a preferred applicator of this invention.
Figure 2:
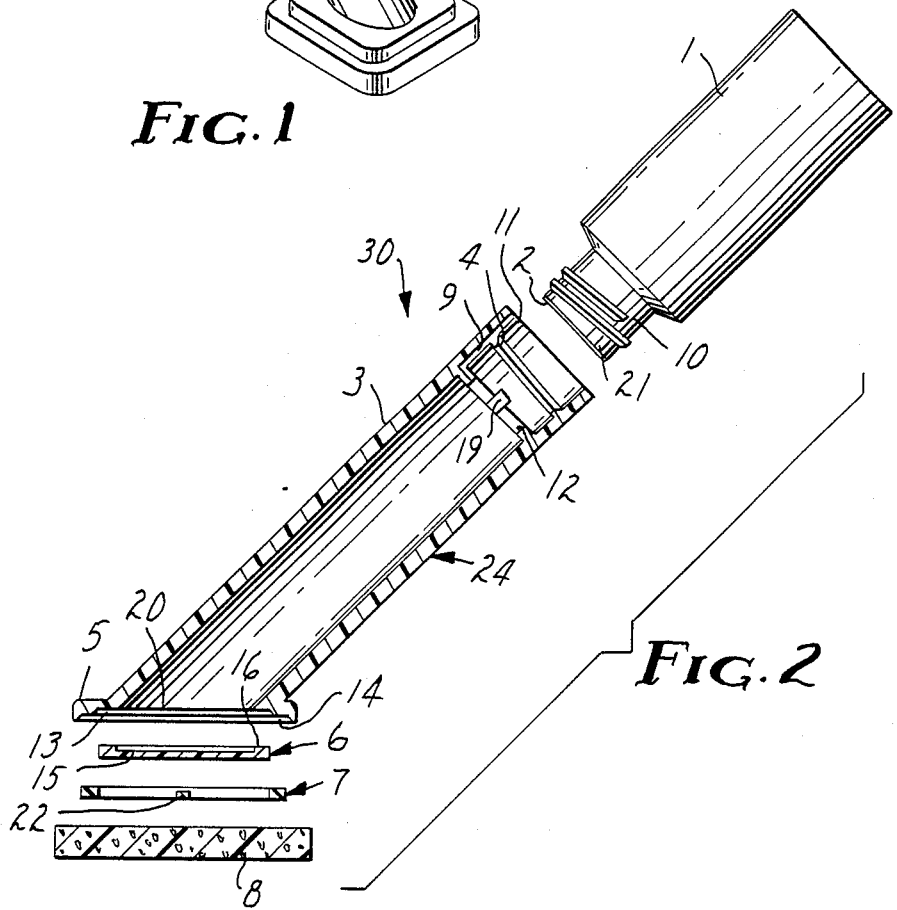
FIG. 2 is a cross-section side view of the various unassembled elements of the preferred applicator of FIG. 1, excluding reservoir 1.

With reference to FIGS. 1 and 2, the applicator 30 includes a reservoir 1 containing the solution to be applied by the applicator, and a hollow elongate member 24 which acts as a handle and a conduit through which the solution passes before it is dispensed by foam sponge 8. Preferably, hollow elongate member 24 is bounded by major orifice 11 at one end and flange 5 at the opposite end. It is constructed so as to include a fixation means 4 adjacent orifice 11 for engaging at orifice 11 reservoir 1, a tubular handle 3 communicating between major orifice 11 and major orifice 20 defined by flange 5, and an air vent 9. Air vent 9 aspirates air into hollow elongate member 24 as liquid flows out through major orifice 20 during the dispensation process, thereby maintaining atmospheric pressure inside the applicator.

A porous metering insert 6 is disposed over major orifice 20 and is sandwiched between the underside of flange 5 and open-cell foam sponge 8. The porous metering insert 6 is disposed over major orifice 20 to control the flow of liquid out of hollow elongate member 24 and into foam sponge 8.

Foam sponge 8 can be selected from a variety of commercially available materials having a wide range of compression set ratios (i.e., density) and porosities. By varying the pore size, void fraction and hydrophilicity of the porous metering insert 6 and the compression set ratio and porosity of the foam sponge 8, applicators can be constructed to apply a variety of solution compositions, viscosities and volumes. The pore size, void volume fraction, and hydrophilicity of porous metering material 6 and the compression set ratio and porosity of open-cell foam sponge 8 are adjusted in relation to the viscosity, volume and surface tension of the liquid to be dispensed to allow a portion of the liquid contained in the applicator to flow to the outer surface of sponge 8 but not to allow the liquid to drip from the open-cell foam sponge 8 when it is suspended in mid-air with flange 5 down. It should be noted that to create a completely dripless applicator the amount of liquid to be dispensed by the device must not exceed the reservoiring capacity of sponge 8.

Metering insert 6 and sponge 8 are held together and disposed over major orifice 20 by a variety of suitable means, including adhesive bonding. In the preferred embodiment, elongate member 24 includes a flange 5 surrounding major orifice 20. The inner portion of flange 5 contains two lips defined by recesses 13 and 14. Metering insert 6 is contained within recess 13 and is held therein by foam sponge insert 8 which is adhered to the outer rim of flange 5 by heat-activatable bonding insert 7.

The invention will now be more particularly described in terms of the following preferred embodiment.

FIG. 1 shows the preferred embodiment fully assembled from each of the parts shown in FIG. 2. The device illustrated in FIG. 1 consists of the following components as shown in FIG. 2: reservoir 1 containing the prep solution and sealed at its major orifice 21 by seal 2; hollow elongate member 24 being threaded at one end to accept reservoir 1, and having an angled flange 5 at the opposite end, and including air vent 9; porous metering insert 6 disposed within flange 5; thermoplastic bonding insert 7 also disposed within flange 5; and foam sponge 8.

Reservoir 1 is preferably a bottle with a threaded opening molded from a thermoplastic material compatible with the prep solution. The preferred embodiment comprises an essentially rigid, high-density polyethylene, cylindrical bottle with threaded portion 10 smaller in diameter than the main body of the bottle. Reservoir 1 is preferably filled and inductively sealed with foil seal 2 using conventional techniques.

Hollow elongate member 24 can be molded from any thermoplastic compatible with the liquid to be dispensed. Preferably, hollow elongate member 24 is molded from medium density polyethylene. Features of the preferred embodiment of this component include tubular handle 3, major orifice 11 which communicates with reservoir 1 at orifice 21 thereof, integrally-formed radially-projecting interior flange 12 which acts as a reservoir seat, integrally-formed fixation means 4 which threadably engages reservoir 1, projecting means 19 to tear seal 2 on reservoir 1, air vent 9, and flange 5 located at the opposite end of hollow elongate member 24 from orifice 11.

For surgical prep applications it is important that tubular handle 3 be long enough to prevent contact of the patient by the person applying the surgical prep solution. Preferably for such applications tubular handle 3 is at least about four inches long.

Figure 3:
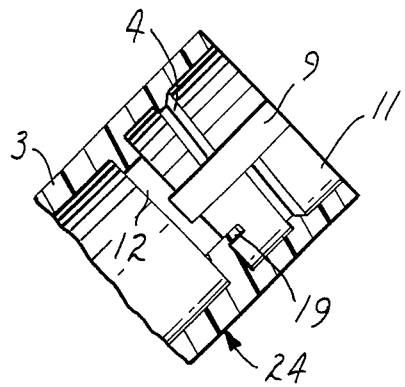
FIG. 3 is a cross-section auxiliary view of the top portion of the hollow elongate member shown in FIG. 2.

Projecting means 19 is positioned within hollow elongate member 24 so as to be capable of puncturing seal 2 on reservoir 1 when reservoir 1 is engaged at orifice 11 by fixation means 4. Many different geometries are possible for projecting means 19. The preferred embodiment, as shown in FIG. 3, includes an integrally-formed projection that first extends radially from integrally-formed radially-projecting interior flange 12 and then extends in a direction towards orifice 11, parallel to the longitudinal axis of elongate member 24. The projection 19 is preferably of a size sufficient to begin rupturing seal 2 after reservoir 1 has been threaded at least one-half turn into hollow elongate member 24, with complete rupturing occuring three-fourth turn thereafter. Other possible embodiments of projecting means 19 include a hollow metal or polymeric spike.

Air vent 9 is a necessary component of the applicator. Metering insert 6 greatly restricts the amount of air which can enter the applicator through orifice 20. In order to avoid creating a vacuum and restricting flow through the device a means of maintaining atmospheric pressure in the device must be employed. Air vent 9 provides such a means. Air vent 9 is preferably an L-shaped slot having its long leg lying parallel to the longitudinal axis of elongate member 24 and recessed through the threads of fixation means 4, and its short leg lying perpendicular to the longitudinal axis of elongate member 24 and recessed through an upper portion of interior flange 12. Preferably, air vent 9 is located on the wall of hollow elongate member 24 which forms an obtuse angle with flange 5. In this manner, the liquid runs down the side of tubular handle 3 which is furthest from air vent 9 when the applicator is inverted in the position shown in FIG. 1. This location of air vent 9 minimizes the potential for leakage when the applicator is moved into position for use.

Further, the short leg of air vent 9 projects only through an upper portion of flange 12, leaving the lower portion of this flange intact and radially projecting into the interior of elongate member 24. In this manner when the applicator is inverted from the position shown in FIG. 1 and the liquid is allowed to flow from tubular handle 3 back into reservoir 1, the liquid cascades over flange 12 and past air vent 9, thereby minimizing the potential for leakage of liquid through air vent 9. As a further means of reducing the potential of leakage, the size of air vent 9 is minimized.

Other geometries and locations of air vent 9 are envisioned by the inventor. For example the air vent could merely comprise a hole through tubular handle 3. Preferably such a hole would not be present in a location which would result in leakage of liquid from the device.

Preferably flange 5 is integrally formed and is angled from the longitudinal axis of elongate member 24 by between about 30 and 90 degrees Most preferably there is about a 45 degree angle between flange 5 and the longitudinal axis of elongate member 24. Flange 5 preferably includes recesses 13 and 14 on its interior surface. Recesses 13 and 14 are dimensioned and shaped to permit nesting therein of metering insert 6 and bonding insert 7, respectively. Preferably recess 14 is greater in area than recess 13 to provide for sandwiching of metering insert 6 between orifice 20 and bonding insert 7.

The distribution and rate of delivery of the liquid to open-cell foam sponge 8 is controlled by porous metering insert 6. For a given volume, viscosity, and surface tension of the liquid, rapid wetting of the foam sponge without dripping can be accomplished by appropriate specification of the average pore size, void volume fraction and hydrophilicity of porous metering insert 6 and the permanent compression set ratio and porosity of open-cell foam sponge 8.

Preferably, the pore size, void volume and hydrophilicity of porous metering insert 6 are adjusted so that for any given volume, viscosity and surface tension of the liquid to be applied the average flow rate of the liquid through metering insert 6 is between about 0.25 and 10 mls/sec. Greater flow rates than this will tend to result in an applicator which drips, while lower flow rates will result in an applicator which does not provide adequate liquid for surgical scrub applications. Most preferably for surgical scrub applications, the average flow rate of liquid through porous metering insert 6 is between, 1 and 5 ml/sec. In general, for lower volumes and/or higher viscosity liquids the pore size and/or void volume of porous metering insert 6 is adjusted upwards to achieve the desired flow rates. Furthermore, as the surface tension of the liquid increases the metering insert is varied from a hydrophobic to a hydrophilic material to achieve the desired flow rate.

Porous metering insert 6 is substantially rigid and can be constructed from either hydrophilic or hydrophobic materials depending upon the liquid to be dispensed. Metering insert 6 unfoamed can be in the form of sintered metal or plastic, molded unfoamed porous plastic, porous plastic films, porous metal structures and porous ceramics. Methods for making such porous structures include well-known sintering or leaching processes. Preferably, porous metering inserts are constructed from ceramics or thermoplastic materials such as polypropylene, polyethylene, polyvinylidene fluoride, ethylene-vinyl acetate copolymers, styrene-acrylonitrile copolymers and polytetrafluoroethylene. The hydrophilicity of the metering insert can be increased by various well-known treatments.

In general, the average pore size of metering insert 6 is between about 1 and 2,000 microns and the void volume is between about 10 and 70 percent. Preferably, for surgical applications where antiseptic solutions are dispensed, the average pore size of the metering insert is between about 10 and 500 microns and the void volume is between about 20 and 60 percent. Most preferably for such applications the average pore size is between about 60 and 100 microns and the void volume is between about 30 and 50 percent. A preferred ceramic material for use as a porous metering insert is 3M Brand Porous Structures ™, commercially available from 3M, Saint Paul, Minnesota. This material has an average pore size of between about 14 and 175 microns and a void volume of approximately 30 percent. A particularly preferred porous metering material is a porous high density polyethylene commercially available as Interflo ® Porous Plastic, F/N35-160-22, from Chromex Chemical Corp., Brooklyn, New York. This material has an average pore size of between about 60 and 100 microns and a void volume of between about 40 and 60 percent.

In general, metering insert 6 is relatively non-reservoiring, having a reservoiring capacity of less than about 5.0 cc/gm, preferably less than about 1.0 cc/gm, and most preferably about 0.7 cc/gm. Fluid which is reservoired in an intermediate flow regulator is not available for application to the surface to be treated. Thus, metering insert 6 provides controlled flow of fluid without significant fluid waste due to retained fluid within the metering insert itself.

Figure 4:
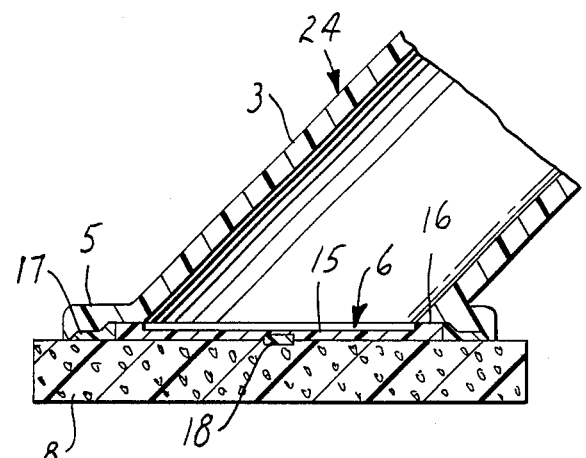
FIG. 4 is a cross-section of the dispensing end of the assembled applicator of FIG. 1.
Figure 5:
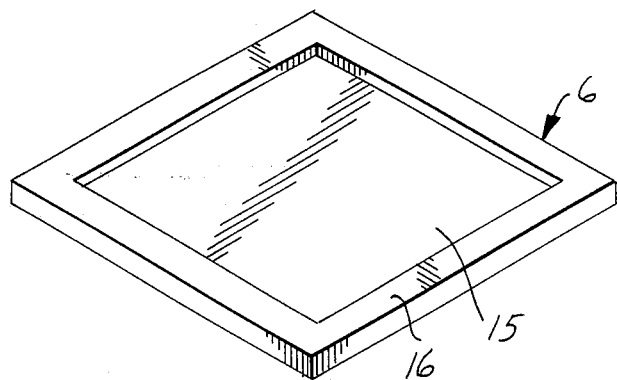
FIG. 5 is a perspective view of a preferred porous metering insert.

As shown most clearly in FIGS. 4 and 5, the preferred embodiment of porous metering insert 6 has an area which is greater than the area of major orifice 20. Preferably, the area of insert 6 is at least two times greater than the area of orifice 20, and is most preferably almost as large as foam sponge 8. The preferred embodiment of metering insert 6 also has a raised periphery 16 which extends above planar metering area 15 and creates a cavity between active metering area 15 and major orifice 20. Preferably, raised periphery 16 extends above planar metering area 15 to the extent of one to two times the thickness of planar metering area 15. Both the increased area of insert 6 and raised periphery 16 serve to increase the area of fluid distribution to open-cell foam sponge 8.

Bonding insert 7 is a gasket-like structure, preferably having a rectangular annular shape. Preferably a bridging member 22 is included between opposing sides of bonding insert 7 to provide structural support to foam sponge 8 and prevent sagging thereof due to the weight of the absorbed fluid to be dispensed.

With reference to FIG. 4, after assembly of the applicator and inductive melting of bonding insert 7, metering insert 6 and foam sponge 8 are peripherally affixed to flange 5 by bond 17, and metering insert 6 and foam sponge 8 are bonded together at bond 18.

Bonding insert 7 can be molded, extruded or die cut from a compatible thermoplastic or heat-activatable material filled with an inductively active material. Examples include laminated composites comprised of metal foil sandwiched between layers of thermoplastic or heat-activatable bonding material, such as polyethylene or hot-melt adhesives. Preferred examples include such thermoplastic or heat-activatable bonding materials filled with an inductive metal or metal oxide powder, e.g., 5 to 50 percent by volume iron powder having an average particle size of from about 300 to 400 mesh. A particularly preferred bonding insert 7 is a rigid gasket formed from injection molded polyethylene filled with about 12 to 15 percent by volume iron powder, commercially available from Emabond Inc., Norwood, New Jersey, as G-10-205.

Open-cell foam sponge 8 comprises an open-cell foam material compatible with the liquid to be dispensed. Suitable open-cell foam sponge materials are prepared from elastomeric thermoplastic materials such as polyethylene and polyurethane. Especially preferred open-cell foam materials are prepared from polyurethane elastomers.

By utilizing a permanently compression-set foam, the wicking and reservoiring properties of the foam sponge 8 can be selected such that the fluid delivered through metering insert 6 wets foam sponge 8 but does not drip from sponge 8 when it is suspended in mid-air with flange 5 down. The greater the compression set ratio, the greater the amount of liquid that can be absorbed by the sponge material. Preferably, the foam sponge material is compression set (i.e., compressed) by heat and pressure to from about 1.5 to 10 times its original density, i.e., the compression set ratio is between about 1.5 and 10. Most preferably the compression set ratio of sponge 8 is between about 2 and 4.

The porosity of the foam sponge material can be selected such that foam sponge 8 will release a uniform amount of liquid when it is lightly rubbed against the surface upon which the liquid is to be dispensed. Preferably, for surgical prep applications, the porosity of the foam sponge material is between about 10 and 100 pores per linear inch, more preferably about 90 pores per linear inch. A particularly preferred open-cell foam sponge material is an elastomeric polyurethane foam having a compression set ratio of between about 2 and 4 and a porosity of about 90 pores per linear inch, commercially available from Scotfoam Corp., Eddystone, Pa., as Scottfelt TM 3-900-Z.

The applicator of this invention is useful in dispensing liquids having viscosities at ambient temperatures of less than about 10,000 cps, most preferably less than about 500 cps.

As noted above, the applicator is useful in dispensing antiseptic liquids to cleanse a surgical field prior to surgery. Examples of suitable antiseptic preparations include those described in U.S. Pat. No. 4,584,192 and those described in U.S. Pat. No. 4,542,012, the disclosures of which are incorporated herein by reference. The antiseptic liquid is placed in the applicator and the applicator head is gently rubbed over the surgical field to thereby cleanse it. The applicator can be handled easily without dripping the liquid onto other articles in the vicinity of the surgical field. The dripless feature allows application of the liquid to only the desired areas of the patient and also allows for quicker and more efficient use of a surgical facility due to elimination of the time needed to clean the facility of the drippings of antiseptic prep.

Although specific embodiments of the invention have been described herein, it is not intended to limit the invention solely thereto, but to include all of the obvious variations and modifications within the spirit and scope of the appended claims.

What is claimed:

1. An article useful as a dispenser for the application of pre-operative surgical scrubs or paints to skin comprising
    (a) a hollow elongate member having a major orifice at one end thereof;
    (b) a layer of unfoamed, rigid, porous metering material disposed over said major orifice, said porous metering material having a reservoiring capacity of less than about 5.0 cc/gm and said layer capable of regulating the flow of liquid therethrough;
    (c) a layer of sponge material having a permanent compression set ratio of about 1.5 to about 10 disposed over the exterior surface of said layer of porous metering material; and
    (d) an air vent in said hollow elongate member capable of providing air flow between the exterior of said hollow elongate member and any solution to be applied by said applicator which is contained in said elongate member.

2. An article accordance with claim 1 wherein said porous metering material is capable of limiting liquid flow therethrough to between about 0.25 and 10 mls/sec.

3. An article in accordance with claim 2 wherein the average pore size of said porous metering material is between about 1 and 2,000 microns.

4. An article in accordance with claim 2 wherein the void volume of said porous metering material is between about 10 and 70 percent.

5. An article in accordance with claim 2 wherein said porous metering material is a high density polyethylene having an average pore size of between about 60 and 100 microns and a void volume of between about 40 and 60 percent.

6. An article in accordance with claim 1 wherein said article further comprises a reservoir containing the solution to be applied by said article, which reservoir is contained within or communicates with said hollow elongate member.

7. An article in accordance with claim 6 wherein said hollow elongate member comprises a second major orifice at the end opposite said first major orifice and a fixation means formed on the interior of said hollow elongate member adjacent said second major orifice, said fixation means capable of engaging said reservoir.

8. An article in accordance with claim 1 wherein
    (a) said hollow elongate member includes a flange disposed at said major orifice, said flange extending radially outward from said major orifice; and
    (b) said layer of porous metering material is disposed adjacent the interior surface of said flange.

9. An article in accordance with claim 8 wherein said flange is disposed so as to form an angle of about 30 to 90 degrees with the longitudinal axis of said hollow elongate member.

10. An article in accordance with claim 1 wherein said sponge material has a porosity of between about 10 and 100 pores per linear inch.

11. An article useful as a dispenser for the application of a liquid to a surface comprising
    (a) a hollow elongate member having a major orifice at one and thereof and a second major orifice at the end opposite said first major orifice; a fixation means formed on the interior of said hollow elongate member adjacent said second major orifice; and a flange projecting radially into the interior of said hollow elongate member, said flange located adjacent said fixation means and spaced from said second major orifice by said fixation means;

(b) a layer of unfoamed porous metering material disposed over said major orifice, said porous metering material having a reservoiring capacity of less than about 5.0 cc/gm and said layer capable of regulating the flow of liquid therethrough;

(c) a layer of sponge material having a permanent compression set ratio of about 1.5 to about 10 disposed over the exterior surface of said layer of porous metering material;

(d) an air vent in said hollow elongate member capable of providing air flow between the exterior and interior of said hollow elongate member, which air vent comprises an L-shaped slot having one leg recessed through said fixation means and the other leg recessed through an upper portion of said flange; and (e) a reservoir containing the solution to be applied by said article which reservoir is contained within or communicates with said hollow elongate member, and which reservoir is engaged by said fixation means.

12. An article useful as a dispenser for the application of a liquid to a surface comprising (a) a hollow elongate member having a major orifice at one end thereof and a flange disposed at said major orifice, said flange extending radially outward from said major orifice and disposed so as to form an angle of about 30 to 90 degrees with the longitudinal axis of said hollow elongate member;

(b) a layer of unfoamed porous metering material disposed over said major orifice adjacent the interior surface of said flange, said porous metering material having a reservoiring capacity of less that about 5.0 cc/gm and said layer capable of regulating the flow of liquid therethrough;

(c) a layer of sponge material having a permanent compression set ratio of about 1.5 to about 10 disposed over the exterior surface of said layer of porous metering material;

(d) an air vent in said hollow elongate member capable of providing air flow between the exterior and interior of said hollow elongate member; and (e) a gasket-like bonding insert disposed between said layer of porous metering material and said layer of sponge material, said bonding insert comprising a thermoplastic or heat-activatable material filled with an inductively active material, and said bonding insert adhered to the periphery of said flange and to said sponge material.

* * * * *

UNITED STATES PATENT AND TRADEMARK OFFICE
CERTIFICATE OF CORRECTION

PATENT NO. : 4,925,327

DATED : May 15, 1990

INVENTOR(S) : David F. Wirt

It is certified that error appears in the above-identified patent and that said Letters Patent is hereby corrected as shown below:

In column 1, lines 39-40, delete "within a tubular handle having one or two No. 4,497,796," and insert --interior spikes. In the device of U.S. Patent No. 4,498,796,--.

Signed and Sealed this

Eleventh Day of June, 1991

Attest:

HARRY F. MANBECK, JR.

Attesting Officer

Commissioner of Patents and Trademarks